US00PP11384P

United States Patent [19]

Carruth

[11] Patent Number: Plant 11,384

[45] Date of Patent: May 16, 2000

[54] HYBRID TEA ROSE PLANT NAMED 'WEKCRYLAND'

[75] Inventor: Thomas F. Carruth, Altadena, Calif.

[73] Assignee: Weeks Wholesale Rose Grower, Inc., Upland, Calif.

[21] Appl. No.: 09/150,071

[22] Filed: Sep. 8, 1998

[51] Int. Cl.[7] ..... A01H 5/00

[52] U.S. Cl. ..... Plt./133

[58] Field of Search ..... Plt./130, 132, 133, Plt./137, 141, 144

*Primary Examiner*—Howard J. Locker

*Attorney, Agent, or Firm*—Christie, Parker & Hale, LLP

[57] ABSTRACT

A new variety of Hybrid Tea rose suitable for garden decoration, having flowers of white coloration with a very fine pink edging.

1 Drawing Sheet

BACKGROUND OF THE INVENTION

This invention relates to a new and distinct variety of Hybrid Tea rose. The varietal denomination of the new variety is 'WEKcryland'. It has as its seed parent the variety known as 'ARObipy' (U.S. Plant Pat. No. 6,714) and as its pollen parent the variety known as 'WEKjoe' (U.S. Plant Pat. No. 9,389).

SUMMARY OF THE INVENTION

Among the features which distinguish the new variety from other presently available and known commercial rose cultivars are the following combination of characteristics: its peduncle bearing many stipitate glands, its large white flowers whose petals usually bear a very fine line of pink edging, its large abundant leaves and its very thorny underside of the leaf rachis. The plant is an upright growing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKcryland' may be asexually propagated by cuttings, budding or grafting.

COMPARISON WITH PARENTS

The new rose may be distinguished from its seed parent, 'ARObipy', by the following combination of characteristics: whereas 'WEKcryland' bears white flowers usually with petals finely edged with pink, 'ARObipy' bears predominantly white flowers. The seed parent has a tall mature growth habit, whereas the new variety has a significantly shorter mature growth habit. 'WEKcryland' bears leaves with a matte finish, whereas 'ARObipy' bears leaves with a semi-glossy finish.

The new variety may be distinguished from its pollen parent, 'WEKjoe', by the following combination of characteristics: whereas 'WEKjoe' bears white flowers with a very broad pink edging on the petals, 'WEKcryland' bears white flowers with a significantly finer pink edging. The pollen parent has a very tall mature plant habit bearing flowers on very long stems, whereas the new variety has a significantly shorter mature plant habit and stem length.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of August. Phenotypic expression may vary with environmental, cultural and climatic conditions, as well as differences in conditions of light and soil.

FLOWER

The new variety usually bears its flowers singly, sometimes in irregularly rounded clusters of two to three per stem, on strong moderately long stems (about 45 to about 70 cms.). Outdoors, the plant blooms abundantly and nearly continuously during the growing season. The flowers have a slight tea to spicy fragrance.

BUD

The peduncle is about 5.5 to about 7 cms. in length, of moderately heavy caliper, and usually erect. It is moderately rough, with very many stipitate glands and some hairs. Peduncle color is between 144A and 137C.

Before the calyx breaks, the bud is about 1.9 to about 2.4 cms. in diameter at the widest point, about 2.4 to about 2.7 cms. in length, and pointed to ovoid in shape. The surface of the bud bears some stipitate glands, usually with slender mostly entire foliaceous parts extending beyond the tip of the bud about ½ or more of its length. Bud color is between 144A and 137C.

The inner surface of the sepals is covered with fine wooly tomentum; sepal margins are lined with many stipitate glands. Sometimes the sepal margin bears a few very slender small foliaceous appendages.

As the petals open (after the calyx breaks), the bud is about 2.4 to about 2.9 cms. in diameter at the widest point, about 3.1 to about 3.5 cms. in length, and very pointed to ovoid in form. The color of the under surfaces of the newly opened petals is between 157C and 155B usually finely edged with between 54B and 63B. The color of the upper surfaces is of similar coloration to the under surface but with a significantly finer line of the edge color. On the upper surface at the point where the petal attaches, there is a very small zone of near 2C in coloration.

BLOOM

When fully open, the bloom ranges from about 10 to about 12.5 cms. in diameter. Petalage is double with about 34 to 42 petals and about 1 to 4 petaloids arranged irregularly. When partially open, the bloom form is high centered to somewhat cupped, and the petals are moderately spiraled to cupped with petal edges somewhat reflexed outward. When fully open, the bloom form is more flat to cupped, and the petals are more loosely spiraled to cupped with petal edges more reflexed outward.

PETALS

The substance of the petals is somewhat heavy and of medium thickness, with upper surfaces somewhat satiny and under surfaces somewhat shiny. The outer petals are very broadly obovate to nearly round in shape with rounded apices. The inner petals are broadly obovate in shape with similar apices.

NEWLY OPENED FLOWER

The under surface of the outer petals is between 157D and 155B usually finely edged with between 55A and 63C. The upper surface of the outer petals is of similar coloration to the outer surface but with a finer line of the edge color. On the upper surface at the point where the petal attaches, there is a very small zone of near 1D in coloration.

The under and upper surface of the intermediate and inner petals is similar in coloration to the under and upper surface of the outer petals but with deeper edge coloration of between 54B and 63B.

The general tonality of the newly opened flower is between 157D and 155B usually finely edged with between 55A and 63C. The center portion of the flower has a darker edge coloration between 54B and 63B.

THREE DAY OLD FLOWER

The under and upper surface of the outer petals is between 155B and 155D usually without any edge coloration. On the upper surface at the point where the petal attaches, there is a very small zone of between 1D and 157C. The white portions of the outermost petals are sometimes lightly suffused with near 1D.

The under and upper surface of the inner petals is similar in coloration to the under and upper surface of the outer petals but usually with an extremely fine line of edge coloration between 55C and 63D. There is no suffusion of green coloration on the inner petals.

The general tonality of the three day old flower is between 155B and 155D. The inner portion of the flower usually shows an extremely fine line of edge coloration between 55C and 63D.

On the spent bloom, the petals usually drop off cleanly.

In August in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (approximately 70) and are arranged regularly about the pistils. The filaments are of varying lengths, most with anthers. Filaments are near 8D in color. The anthers are moderately small for the class and all open approximately at the same time. Anther color is near 18A when immature and near 165B at maturity. Pollen is moderate to abundant and near 8A in color.

FEMALE REPRODUCTIVE ORGANS

Pistils vary in number (approximately 110). The styles are moderately uneven, varying from short to medium in length somewhat thin in caliper, and loosely bunched. Stigma color is between 11C and 8C. Style color is near 11C moderately suffused with near 47B nearing the style. Ovaries are usually all enclosed in the calyx, although a few may protrude from the calyx.

Hips are of moderately long length, somewhat oblong to pear-shaped in form, and near 24A in color when ripe. The hip surface is moderately smooth with very thick fleshy walls. The sepals persist. There are approximately 12 to 23 moderately large seeds.

FOLIAGE

The compound leaves are usually comprised of three to five or more leaflets and are borne very abundantly. The leaves are about 10.5 to about 17 cms. in length and about 10.5 to about 13.5 cms. in width at the widest point, moderately heavy to somewhat leathery in texture, and matte in finish. The terminal leaflets are about 6 to about 8 cms. in length and about 4 to about 5.5 cms. in width at the widest point, ovate in shape with acute to somewhat acuminate apices and rounded to slightly acute bases. Their margins are usually doubly serrate.

The upper surface of the mature leaf is between 137A and 139A. The under surface of the mature leaf is between 148B and 191A. The upper surface of the young leaf is between 144A and 137B, sometimes suffused with between 183B and 187B. The under surface of the young leaf is between 146C and 144B, often heavily suffused with between 183D and 187D. The veination on the underside of the leaves is very pronounced from the surface.

The rachis is average in caliper and very rough. The upper side is somewhat shallowly grooved with many hairs and stipitate glands on the edges of the grooves. The under side of the rachis is very rough with some hairs and stipitate glands and many (about 4 to about 7) small prickles of varying sizes.

The stipules are about 1.6 to about 1.9 cms. in length with somewhat wide moderately long straight points that usually turn out at an angle of more than 45 degrees.

The plant displays an average degree of resistance to powdery mildew and rust as compared to other commercial varieties grown under comparable conditions in Upland, Calif.

GROWTH

The plant has an upright medium height to tall growth habit (about 120 to about 150 cms. in height and about 80 to about 100 cms. spread at the widest point), with very full branching. It displays very vigorous growth and the canes are medium to heavy caliper for the class.

The color of the major stems is between 146A and 147B. They bear several large prickles which are about 0.6 to about 1 cms. in length. The large prickles are almost straight angled moderately downward to slightly hooked with a somewhat short to medium length broad to nearly rounded base; prickle color is between 165B and 166C. The major stem bears few small prickles of similar shape and coloration.

The color of the branches is between 146B and 144A. The bottom third of the branches is sometimes lightly suffused with near 181D. The branches bear several large prickles that are of similar size and shape to the large prickles on the major stems; prickle color is between 160B and 162C. They bear some small prickles of similar shape and coloration.

The color of the new shoots is between 144A and 146C often suffused with between 181C and 185C. They bear several large prickles that are of similar size and shape to the large prickles on the major stems; prickle color is between 181A and 185B. The shoots bear some small prickles of similar shape and coloration.

I claim:

1. A new and distinct rose plant of the variety substantially as described and illustrated herein.

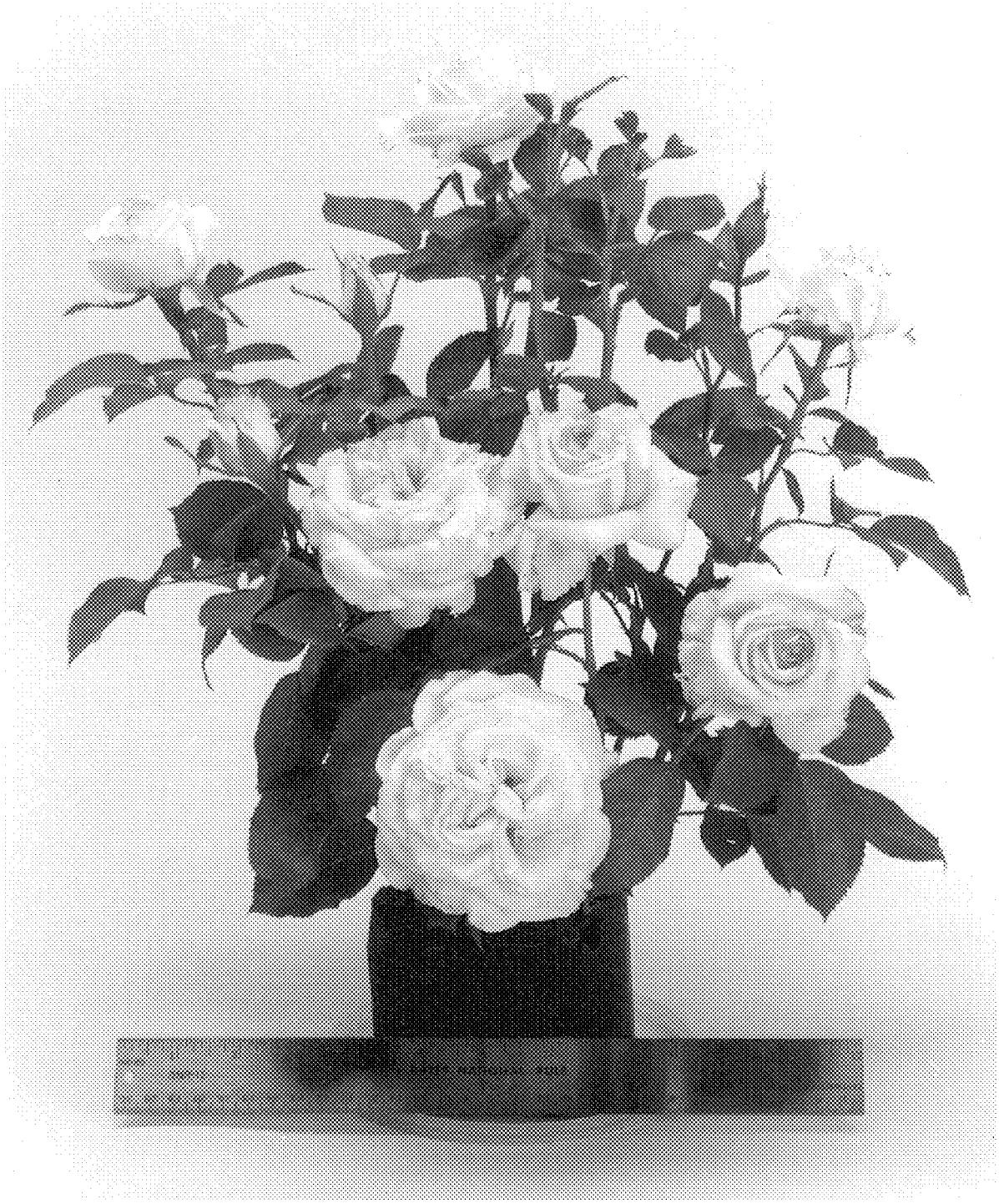

* * * * *